United States Patent [19]

Harvey, deceased et al.

[11] 4,442,216

[45] Apr. 10, 1984

[54] CONTINUOUS ENZYMATIC REACTOR FOR USE OF IMMOBILIZED ENZYME BEADS

[76] Inventors: Douglas G. Harvey, deceased, late of Baltimore, Md.; by Dolores C. Harvey, executrix, 220 Ridgewood Rd., Baltimore, Md. 21210; Christian D. Harvey, 220 Ridgewood Rd., Baltimore, Md. 21210

[21] Appl. No.: 427,879

[22] Filed: Sep. 29, 1982

[51] Int. Cl.³ ............... C12M 1/40; C12N 11/00; C12N 11/14

[52] U.S. Cl. .................. 435/288; 435/174; 435/176

[58] Field of Search ............. 435/288, 174, 176, 264

[56] References Cited

U.S. PATENT DOCUMENTS

| | | | |
|---|---|---|---|
| 3,956,065 | 6/1976 | Idaszak et al. | 435/176 |
| 4,032,407 | 6/1977 | Scott et al. | 435/176 |
| 4,087,330 | 5/1978 | Gregory et al. | 435/176 |
| 4,250,260 | 2/1981 | Rohrbach et al. | 435/176 |
| 4,279,998 | 7/1981 | Shahani et al. | 435/176 |

*Primary Examiner*—David M. Naff
*Assistant Examiner*—Marianne S. Minnick
*Attorney, Agent, or Firm*—John F. McClellan, Sr.

[57] ABSTRACT

Continuous reaction with immobilized enzyme beads is carried out in an enzymatic reactor providing for continuous reaction accompanied by continuous cleansing of the immobilized enzyme beads and continuous recycling of the cleansed-immobilized enzyme beads for reaction. The reactor comprises a reaction chamber having a screw mounted coaxially within a shell having first and second ends, means at the first end for introducing immobilized enzyme beads and fluid reactant material, means at the second end for removal of product, means at the second end for lifting of immobilized enzyme beads and dropping them through a reaction chamber and means for conveying cleansed immobilized enzyme beads from the cleansing chamber to the means for introducing.

15 Claims, 2 Drawing Figures

CONTINUOUS ENZYMATIC REACTOR FOR USE OF IMMOBILIZED ENZYME BEADS

FIELD OF THE INVENTION

This invention relates generally to production systems and specifically to a continuous enzymatic reactor system.

BACKGROUND OF THE INVENTION

The advent of immobilization of enzymes on substrata of gelatin, glass, plastic or ceramic beads has greatly increased the potential for industrial production of organic chemicals, drugs, fuels and a host of other products. The vertical packed-bed reactors currently used in such reactions last a maximum of 750 hours due to microbial action and/or undesirable buildup of foreign substances on the bed.

Generated by living cells, enzymes are non-living proteins which serve as catalysts to convert the food of the cell into energy and a by-product which is discharged by the cell. They are true catalysts in that they induce a chemical change in a substance but are themselves unchanged. They are reaction specific in that a single enzyme reacts with a specific substance and produces a specific product. Thus enzymatic reactions are very specialized and produce highly pure products. Generally, enzymatic reactions take place over a narrow range of pH and temperature.

It is the reaction of enzymes which cause biological reactions to take place. Bacteria, yeasts, and fungi perform chemical transformations because of the enzymes they possess which enable them to digest a substance and produce a waste product, e.g., in the case of yeast, glucose is consumed and ethyl alcohol is produced as the waste product.

Recent developments in this field permit the separation of the enzyme from the cell itself and the attachment of that enzyme onto an inert substrate. The attachment may be of three types: adsorption on glass or ceramic beads; entrapment in a material such as starch or silica gel; and covalent attachment to glass or polymer. In this way, a highly concentrated enzyme is "immobilized" on an inert substance. This enzyme can then perform the desired catalysis in the absence of a living biological species.

This concept is now being used in commercial applications. Eight billion pounds per year of high-fructose corn syrup is being commercially produced using immobilized enzymes. Many other immobilized enzyme production processes are now entering the market place.

The reaction vessels in which these processes take place are either batch type reactors, or more recently, packed-bed reactors. This latter type consists of hollow columns packed with ceramic or glass beads. Feedstock enters the bottom of the column under pressure and product is extracted from the top. The life of the immobilized enzyme is limited by: crushing the beads under pressure; bacterial or microbial clogging of the surface of the beads, or other substances such as impurities or foreign substances in the feed adhering to the surface of the beads and reducing the reactivity of the enzyme. Typical life of the adsorbed immobilized-enzyme glass or ceramic bead ranges from tens of hours up to about 700 hours. Actually, reactivity is being constantly reduced furing the process. When it reaches the point of significant decrease in yield, the column is put out of service, emptied, and repacked with fresh immobilized enzyme beads, a relatively expensive and time consuming process which interrupts production.

SUMMARY OF THE INVENTION

A principal object of this invention therefore is to make available a system which can eliminate drawbacks of presently known cell-separated enzymatic reactors by providing for continuous reaction accompanied by continuous recycling of cleansed-immobilized enzyme beads (or the like particulate matter) through the reaction chamber, and, when desired, by introduction of fresh beads carrying fresh immobilized enzyme material, and by removal of equivalent quantities of spent material.

Further objects are to provide a system as described which is totally enclosed and can produce a high-purity product more reliably and economically than heretofore available.

BRIEF DESCRIPTION OF THE DRAWINGS

The above and other objects and advantages of this invention will become more readily apparent on examination of the following description, including the drawings in which like reference numerals refer to like parts.

DETAILED DESCRIPTION

Figure 1:
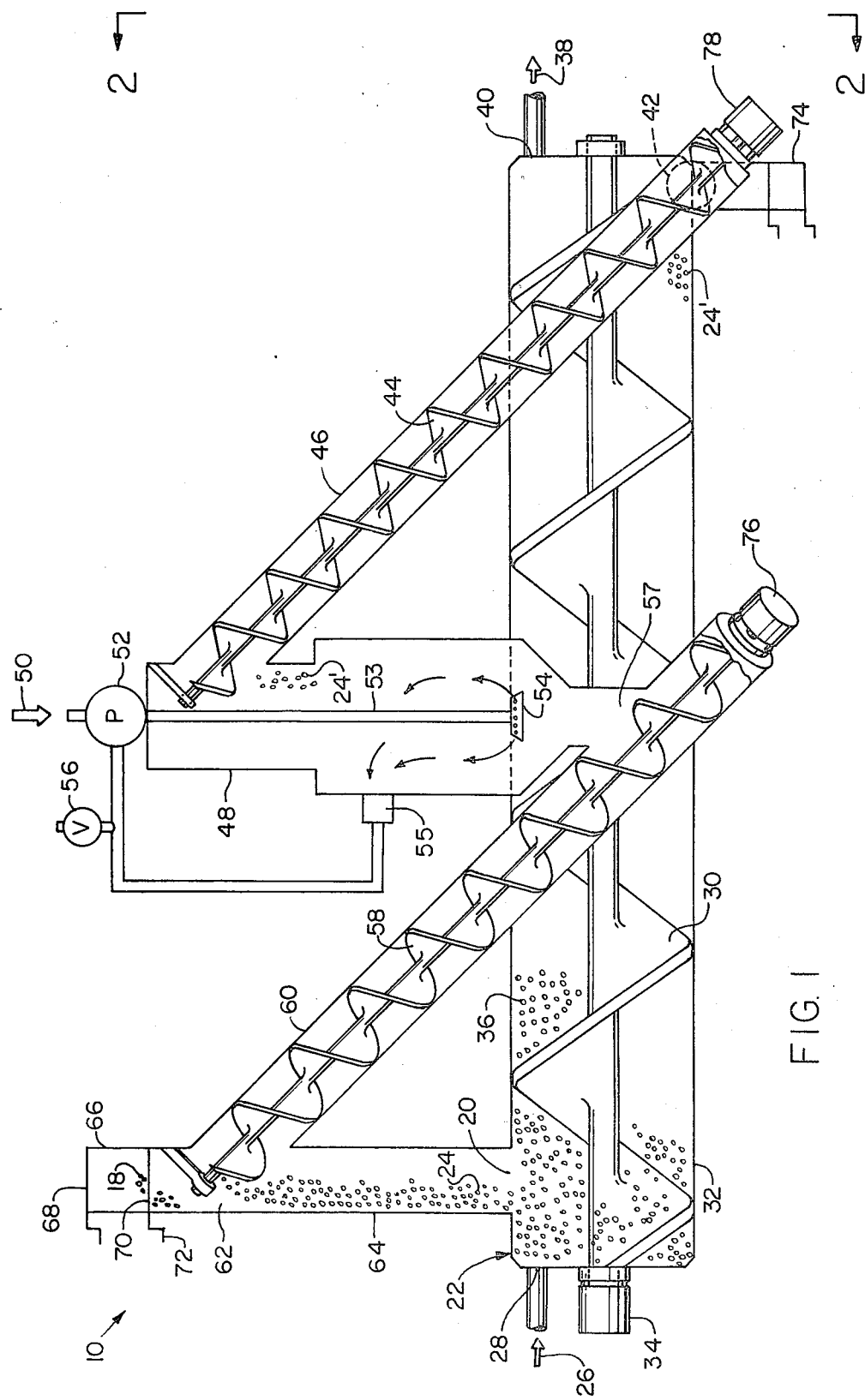
FIG. 1 is a side elevational diagrammatic view.
Figure 2:
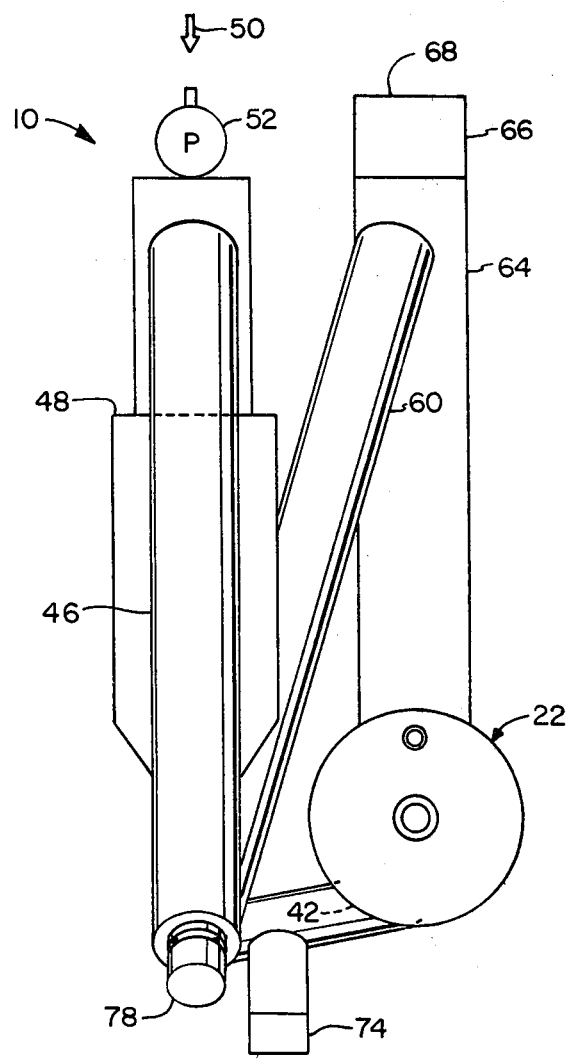
FIG. 2 is an end elevational diagrammatic view taken at 2—2, FIG. 1.

FIGS. 1 and 2 show the continuous enzymatic reactor system invention embodiment 10. A process example is given for conversion of corn sugar to high fructose corn syrup employing the enzyme glucose isomerase.

A first input port 20 in the top of the horizontally disposed basic reactor 22, connecting with reservoir 64, introduces freshly cleaned immobilized-enzyme beads 24 to the basic reactor; in this example glucose isomerase is immobilized on the beads.

At the same time the basic reactor 22 receives fluid reactant feed 26 (corn syrup for example) through second input port 28. Continuously turning main transporter auger 30 coaxially mounted in the cylindrical reactor shell 32 and driven by motor 34 continuously mixes the beads in the basic reactor 22 with the reactant feed and agitates the mix 36. Through third input port 70 in the top of reservoir 64 new beads with the same type immobilized enzyme thereon may be introduced, and are indicated at 18.

Length of the reactors and speed of rotation of the auger are easily made such that the reaction is terminable at the second end of the reactor at the optimum economic point in view of the temperature and pressure employed.

Product 38 high fructose corn syrup in this example being lighter in weight than the beads discharges from the basic reactor at discharge port 40, and the debris coated beads 24' leave the basic reactor at lower exit port 42. From there a first screw lift mechanism 44 continuously transports them up first inclined passage 46 and drops them into vertically disposed cleansing chamber 48. The cleansing chamber may, for compactness of the whole system, be located near the midpoint of the reactor.

In the cleansing chamber 48 the beads are washed by a continuously operating cleansing fluid 50 (arrow)

introduced through pump 52 down third input port or pipe 53 through sprayhead 54, centrally disposed in the lower part of the cleansing chamber 48, and then upwardly directed to exhaust port 55. Exhaust port 55 is located at an upper portion of the cleansing chamber on the opposite side but substantially below the entry point of the beads, and below the discharge point of the beads at the next stage, to prevent overflow. A drain valve 56 may be provided to carry off overflow.

The counterflow of cleansing fluid is made such as to produce substantial agitation to enhance the cleansing action.

The beads exit the cleansing chamber at the lower end 57 of the cleansing chamber where a second screw lift mechanism 58 raises them up a second inclined passage 60 to the top 62 of the entry port reservoir 64. This location is substantially above the cleansing fluid discharge port, to provide bead drainage and prevent overflow.

The new beads carrying fresh immobilized enzyme can be introduced at a lock-out chamber 66 above the reservoir 64 by a conventional passbox with serial doors 68, 70 operable in sequence from the outside as at crank 72 which pivots them. Old beads may be removed through a similar lockout chamber 74 below the lower exit port 42. Thus, if for any reason, it is necessary to change beads, such change can be accomplished during system operation. No shut-down is required.

Clearance between the screws and the walls of the housings coaxial with them is made less than bead size to prevent backflow, jamming, or bead or screw damage. Practical bead sizes may therefore range from one millimeter up, depending on size of the apparatus, which sets feasible manufacturing tolerances.

Conventional electric motors 76, 78 may be used for continuously turning the screw lift mechanisms.

This invention is not to be construed as limited to the particular forms disclosed herein, since these are to be regarded as illustrative rather than restrictive. It is, therefore, to be understood that the invention may be practiced within the scope of the claims otherwise than as specifically described.

What is claimed and desired to be protected by United States Letters Patent is:

1. A continuous enzymatic reactor for use of immobilized enzyme beads to act on a fluid reactant material and to produce a product lighter in weight than said immobilized enzyme beads comprising a basic reactor having first and second ends, a screw, a shell, the screw mounted coaxially within the shell; means for introducing cleansed immobilized enzyme beads continuously to the basic reactor at said first end, means for feeding fluid reactant material into the basic reactor at said first end, means for continuously mixing, agitating and transporting said immobilized enzyme beads and fluid reactant material by rotating said screw; means at said second end for removing product produced; a cleansing chamber, means for lifting the immobilized enzyme beads continuously from said second end and dropping them through said cleansing chamber; means for cleansing the immobilized enzyme beads continuously during said dropping, and means for conveying the cleansed immobilized enzyme beads continuously from the cleansing chamber to said means for introducing.

2. In a reactor as recited in claim 1, said basic reactor being horizontal.

3. In a reactor as recited in claim 2, said means for introducing including said basic reactor having a first port located above said first end.

4. In a reactor as recited in claim 3, said first port having a reservoir thereabove.

5. In a reactor as recited in claim 4, a lock-out chamber above said reservoir for introducing new immobilized enzyme beads with enzymes attached thereto.

6. In a reactor as recited in claim 3, said means for feeding fluid reactant material including a second port at said first end adjacent to said first port.

7. In a reactor as recited in claim 2, said means for lifting located for lifting said immobilized enzyme beads from a position below said second end.

8. In a reactor as recited in claim 7, said means for removing product being higher than said position below said second end.

9. In a reactor as recited in claim 7, a lock-out chamber below said second end adjacent to a portion of said means for lifting.

10. In a reactor as recited in claim 7, said cleansing chamber being vertical.

11. In a reactor as recited in claim 10, said cleansing chamber being at a location intermediate the length of said basic reactor.

12. In a reactor as recited in claim 11, said means for lifting inclining at an angle upwardly to an upper part of said cleansing chamber.

13. In a reactor as recited in claim 10, said means for cleansing including said cleansing chamber having a fluid intake at a lower portion thereof and a fluid exhaust at an upper portion thereof for producing a counterflow of fluid on immobilized enzyme beads dropping through said chamber.

14. In a reactor as recited in claim 13, said means for conveying inclining at an angle upwardly to an upper portion of said means for introducing and conveying said cleansed immobilized enzyme beads from a point below said cleansing chamber.

15. In a reactor as recited in claim 13, said means for lifting inclining upwardly to an upper part of said cleansing chamber, and said fluid exhaust being below said upper part.

* * * * *